US008853172B2

(12) United States Patent
Masuta et al.

(10) Patent No.: US 8,853,172 B2

(45) Date of Patent: Oct. 7, 2014

(54) ANTI-PLANT-VIRUS AGENT

(75) Inventors: Chikara Masuta, Sapporo (JP); Hanako Shimura, Sapporo (JP); Shinsuke Sano, Chigasaki (JP); Takako Fukagawa, Odawara (JP)

(73) Assignees: National University Corporation Hokkaido University, Hokkaido (JP); Nippon Soda Co., Ltd., Tokyo (JP)

( * ) Notice: Subject to any disclaimer, the term of this patent is extended or adjusted under 35 U.S.C. 154(b) by 9 days.

(21) Appl. No.: 13/394,395

(22) PCT Filed: Sep. 9, 2010

(86) PCT No.: PCT/JP2010/065500

§ 371 (c)(1), (2), (4) Date: Mar. 6, 2012

(87) PCT Pub. No.: WO2011/030816

PCT Pub. Date: Mar. 17, 2011

(65) Prior Publication Data

US 2012/0172580 A1 Jul. 5, 2012

(30) Foreign Application Priority Data

Sep. 14, 2009 (JP) ................................. 2009-211649

(51) Int. Cl.

| | |
|---|---|
| ***A61K 31/34*** | (2006.01) |
| ***A61K 31/70*** | (2006.01) |
| ***A01N 57/16*** | (2006.01) |
| ***A01N 43/08*** | (2006.01) |
| ***A01N 43/16*** | (2006.01) |

(52) U.S. Cl.

CPC ................ *A01N 43/08* (2013.01); *A01N 57/16* (2013.01); *A01N 43/16* (2013.01)

USPC ............................................ 514/25; 514/474

(58) Field of Classification Search

USPC ....................... 536/4.1; 549/315; 514/25, 474

See application file for complete search history.

(56) References Cited

U.S. PATENT DOCUMENTS

| | | | | |
|---|---|---|---|---|
| 5,616,611 | A * | 4/1997 | Yamamoto et al. | 514/474 |
| 6,248,905 | B1 * | 6/2001 | Fujinami et al. | 549/315 |
| 6,420,419 | B1 * | 7/2002 | Suzuki et al. | 514/474 |
| 2007/0025945 | A1 | 2/2007 | Liao et al. | |
| 2008/0188553 | A1 | 8/2008 | Roomi | |

FOREIGN PATENT DOCUMENTS

| | | | |
|---|---|---|---|
| CN | 1176760 | A | 3/1998 |
| CN | 1247869 | A | 3/2000 |
| CN | 1615819 | A | 5/2005 |
| EP | 1932530 | A1 | 6/2008 |
| JP | 10-298174 | | 11/1998 |
| JP | 11-001487 | A | 1/1999 |
| JP | 2000-226398 | | 8/2000 |
| JP | 2000-351905 | | 12/2000 |
| JP | 2001-508808 | | 7/2001 |
| JP | 2001-354522 | | 12/2001 |
| JP | 2005-514046 | | 5/2005 |
| JP | 2005-343880 | | 12/2005 |

OTHER PUBLICATIONS

Murata, Akira, et al., "The Relationship between the Structure and Phage-Inactivating Activity of $_L$-Ascorbic Acid Derivatives", Vitamins (Japan), 1987, vol. 61, Nos. 5-6, pp. 199-204.

Mtyamoto, Setsu, et al., "Effect of Ascorbic Acid Supply on the Response of *Nicotiana rustica* Plants to Tobacco Mosaic Virus Infection", Ann. Phytopath. Soc. Japan, 1980, vol. 46, No. 3, pp. 361-363.

International Search Report issued for PCT/JP2010/065500, dated Oct. 5, 2010, 4 pages (with English translation).

Office Action in Chinese Patent Application No. 201080039637.1, dated Nov. 19, 2013 (English translation).

Office Action kn Japanese Patent Application No. 2011-530867, dated Jan. 7, 2014 (English translation).

EP Communication with a Supplementary European Search Report issued in EP Appln. No. 10815411.3, dated Apr. 8, 2014, 11 pages.

Hosoe et al., "Lepidepyrone, a New y-Pyrone Derivative, from *Neolentinus lepideus*, Inhibits Hyaluronidase", J. Antibiot, Vol, 60, No. 6, pp. 388-390, Jan. 2007.

Hancock et al., "Ascorbic Acid Conjugates Isolated From the Phloem of Cucurbitaceae", Phytochemistry, vol. 69, No. 9, pp. 1850-1858, Jun. 2008.

Yoo et al., "Skin Penetration and Retention of L-Ascorbic Acid 2-Phosphate Using Multilamellar Vesicles", Archives of Pharmacal Research, vol. 31, No. 12, pp. 1652-1658, Dec. 2008.

Kidwai et al., "Green Enzymatic Synthesis of L-Ascorbyl Fatty Acid Ester: An Antioxidant", Synthetic Communications, vol .39, No. 7, pp. 1143-1151, Jan. 2009.

Hiroshi et al., "L-Ascorbic Acid Sulfate Esters with Special Reference to Enzymic Hydrolysis", XP002722016, Journal of Biochemistry, (1974), 75(4), 861-6.

Lee Eldon C. H., "Synthesis of L-Ascorbic Acid and its 2-Phosphate and 2-Sulfate Esters and its Role in the Browning of Orange Juice Concentrate", XP002722017, ACS Symposium Series (1994), 546 (Food Phytochemicals for Cancer Prevention l), 388-400.

March Steven C., "Aspects of the Synthesis, Analysis, and Occurrence of Ascorbate-2-Sulfate and Its Metabolism in Rats", XP002722018, (1973), 135 pp. Avail.: Univ. MicrofilmsAnn Arbor, Mich., Order No. 73-23, 280.

* cited by examiner

*Primary Examiner* — Elli Peselev

(74) *Attorney, Agent, or Firm* — Kenyon & Kenyon, LLP

(57) ABSTRACT

The present invention provides an anti-plant virus agent which exhibits preventative and therapeutic effects on plant virus diseases. The anti-plant virus agent of the present invention is characterized by containing at least one compound selected from the group consisting of ascorbic acid derivatives represented by Formula (I) (wherein, $R^1$ to $R^4$ each independently represents a hydrogen atom, —$SO_3H$, —$PO_3H_2$, a glycosyl group, or —$COR^{11}$, wherein $R^{11}$ represents an unsubstituted or substituted C1-30 alkyl group, or an unsubstituted or substituted C2-30 alkenyl group, with the proviso that $R^1$ to $R^4$ may not all be hydrogen atoms at the same time), and salts thereof.

(Formula I):

OR²
R¹O
O
O
R³O
OR⁴

9 Claims, No Drawings

ANTI-PLANT-VIRUS AGENT

CROSS-REFERENCE TO RELATED APPLICATIONS

This application is a national phase application of PCT/JP2010/065500 filed on Sep. 9, 2010, which claims priority under 35 U.S.C. 119 to Japanese Patent Application No. 2009-211649 filed on Sep. 14, 2009.

TECHNICAL FIELD

The present invention relates to an anti-plant virus agent. More specifically, the present invention relates to an anti-plant virus agent which exhibits preventative and therapeutic effects on plant virus diseases showing symptoms such as yellow mosaic of new leaves, leaf curling, or plant stunting.

BACKGROUND ART

Plants which are grown on agricultural land or general households are often infected with plant viruses, and as a result, the value of commodities, production amounts and appearance, and the like, as an agricultural crop, may be remarkably decreased. Plant virus diseases may cause serious damage to important crops such as grains, vegetables, and fruit trees. Viruses which have invaded plant cells proliferate entirely relying on the metabolisms of the host plants. For this reason, it is difficult to specifically inhibit only the proliferation of the viruses whilst maintaining the normal metabolic pathways in plants. Therefore, plant virus diseases have been diseases which are difficult to be controlled.

Several control agents against plant virus diseases have been proposed. For example, Patent Literature 1 discloses a composition which contains antibacterial antibiotics such as neomycin sulfate and organic acids such as ascorbic acid, and states that the composition is capable of inhibiting plant diseases. In addition, in Patent Literature 1, the ascorbic acid is used for playing a role in assisting the antibacterial substances.

However, anti-plant virus agents which have been proposed hitherto have problems such as in the productivities thereof, in actual inhibitive effects against plant diseases, and safety in animals and plants, and most of them have not been put to practical use. In addition, while anti-plant virus agents which exhibit preventive effects have been proposed, very few anti-plant virus agents which exhibit therapeutic effects have been proposed.

On the other hand, ascorbic acid (vitamin C) or ascorbic acid derivatives have been used for medicines, cosmetics, food, and feedstuffs, and the like. In addition, the use thereof in the prevention of blemishes or freckles, and the like, from a suntan, and the use thereof as a hair growth agent have been proposed (refer to Patent Literatures 2 and 3). However, use of ascorbic acid derivatives for controlling plant diseases is not known.

CITATION LIST

Patent Literature

[Patent Literature 1] PCT Japanese Translation Patent Publication No. 2001-508808

[Patent Literature 2] Japanese Unexamined Patent Application Publication No. 2000-351905

[Patent Literature 3] Japanese Unexamined Patent Application Publication No. 2001-354522

SUMMARY OF INVENTION

Technical Problem

The object of the present invention is to provide an anti-plant virus agent which exhibits preventative and therapeutic effects on plant virus diseases.

Solution to Problem

As a result of intensive studies to solve those problems, the present inventors have found that when ascorbic acid, which has a low antiviral activity and which also had been used only for playing a role in assisting antimicrobial compounds or antibiotics as a main component, is esterified or glycosylated with a specific compound, the compound has a high anti-plant viral activity. The present invention has been completed by further studies based on these findings.

That is, the present invention is directed to an anti-plant virus agent which contains at least one compound selected from the group consisting of ascorbic acid derivatives represented by Formula (I) and salts thereof:

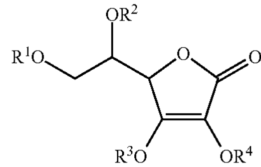

wherein, $R^1$ to $R^4$ each independently represents a hydrogen atom, —$SO_3H$, —$PO_3H_2$, a glycosyl group, or —$COR^{11}$, wherein $R^{11}$ represents an unsubstituted or substituted C1-30 alkyl group, or an unsubstituted or substituted C2-30 alkenyl group, with the proviso that $R^1$ to $R^4$ may not all be hydrogen atoms at the same time.

It is preferable that in Formula (I), $R^1$ and $R^2$ represent a hydrogen atom, and $R^3$ and $R^4$ each independently represents a hydrogen atom, —$SO_3H$, —$PO_3H_2$, a glycosyl group, or —$COR^{11}$, wherein $R^{11}$ represents the same meaning as described above.

In addition, it is also preferable that in Formula (I), $R^1$ be —$COR^{11}$, wherein $R^{11}$ represents the same meaning as described above, and $R^2$ to $R^4$ represent a hydrogen atom.

Advantageous Effects of Invention

The anti-plant virus agent of the present invention has a high anti-plant viral activity. The application of the anti-plant virus agent of the present invention to normal plants makes it possible to effectively prevent infection by plant viruses (preventive effect). In addition, the application of the anti-plant virus agent of the present invention to plants infected with plant viruses makes it possible to suppress the onset of plant diseases (therapeutic effect).

DESCRIPTION OF EMBODIMENTS

Hereinafter, the present invention will be described in detail.

The anti-plant virus agent of the present invention contains at least one compound selected from the group consisting of the ascorbic acid derivative represented by Formula (I) and the salts thereof. In addition, the ascorbic acid derivative of the present invention has a meaning of embracing any one of two isomers of L-ascorbic acid derivatives and isoascorbic acid derivatives, or a mixture thereof.

The ascorbic acid derivatives used in the present invention are those in which in Formula (I), $R^1$ to $R^4$ each independently represents a hydrogen atom, —$SO_3H$, —$PO_3H_2$, a glycosyl group, or —$COR^{11}$ with the proviso that $R^1$ to $R^4$ may not all be hydrogen atoms at the same time.

A glycosyl group is a sugar residue such as a monosaccharide or a low-molecular-weight oligosaccharide (specifically, a partial structure of the molecule containing a binding position formed by the removal of a hemiacetal hydroxyl group of the sugar moiety). Examples of the monosaccharide include glucose, galactose, fructose, and rhamnose, and the like, and examples of the oligosaccharide include rutinose, vicianose, lactose, maltose and sucrose, and the like. Therefore, the glycosyl group includes, for example, a glucosyl group, a galactosyl group, a fructosyl group, and a rhamnosyl group, and the like. In addition, the glycosyl group also includes the groups forming disaccharides by the binding of any combination of these glycosyl groups via 1→2 linkage, 1→3 linkage, 1→4 linkage or 1→6 linkage.

$R^{11}$ represents an unsubstituted or substituted C1-30 alkyl group, or an unsubstituted or substituted C2-30 alkenyl group.

Herein, the term "unsubstituted" means that the relevant group has only a group forming a mother nucleus. In addition, descriptions using only the name of the group forming a mother nucleus without the expression "substituted", unless otherwise stated, mean "unsubstituted".

On the other hand, the term "substituted" means that the hydrogen atom of any of the group forming a mother nucleus is replaced with a group which has a different structure from that of the mother nucleus. Therefore, the term "substituent" refers to another group which replaces a group forming a mother nucleus. There may be one or two or more substituents. The two or more substituents may be the same as or different from each other. For example, a substituted C1-30 alkyl group is one in which a group Banning a mother nucleus is a C1-30 alkyl group, and any hydrogen atom of this group is substituted with a group having a different structure (the "substituent").

The C1-30 alkyl group is a saturated aliphatic hydrocarbon group having 1-30 carbon atoms. The C1-30 alkyl group may be a straight chain or a branched chain.

Specifically, a methyl group, an ethyl group, an n-propyl group, an isopropyl group, an n-butyl group, an isobutyl group, an s-butyl group, a t-butyl group, an n-pentyl group, an n-octyl group, an n-undecyl group, an n-tetradecyl group, an n-pentadecyl group, an n-hexadecyl group, an n-henicosyl group, an n-triacontyl group, and the like, can be exemplified.

The C2-30 alkenyl group is an aliphatic hydrocarbon group having 2 to 30 carbon atoms and having at least one carbon-carbon double bond. The C2-30 alkenyl group may be a straight chain or a branched chain.

Specifically, a vinyl group, a 1-propenyl group, an allyl group, a 1-hexenyl group, a 2-hexenyl group, a 3-hexenyl group, a 4-hexenyl group, a 5-hexenyl group, a 2-pentadecen-8-yl group, and the like, can be exemplified.

Examples of the groups which can be a "substituent" of the C1-30 alkyl group or the C2-30 alkenyl group include a hydroxyl group; a mercapto group; an amino group; a nitro group; a halogen atom such as a chlorine atom, a fluorine atom or a bromine atom; an alkoxy group such as a methoxy group, an ethoxy group, an isopropoxy group, an n-propoxy group, an n-butoxy group, an isobutoxy group, an s-butoxy group or a t-butoxy group; an aryloxy group such as a phenoxy group or 1-naphthyloxy group; a haloalkoxy group such as a fluoromethoxy group, a difluoromethoxy group, trifluoromethoxy group, a 2-chloroethoxy group, a 2,2,2-trichloroethoxy group or a 1,1,1,3,3,3-hexafluoro-2-propoxy group; an alkylthio group such as a methylthio group or an ethylthio group; an arylthio group such as a phenylthio group or a 1-naphthylthio group; an alkylamino group such as a methylamino group or a diethylamino group; an arylamino group such as an anilino group or a 1-naphthylamino group; and a cyano group, and the like.

The above $R^{11}$ is preferably an unsubstituted or substituted C8-20 alkyl group, or an unsubstituted or substituted C8-20 alkenyl group. More preferred as $R^{11}$ are an n-pentyl group, an n-hexadecyl group, an n-heptadecyl group, an n-octadecyl group, and a 9-hexadecenyl group.

One kind of the preferred ascorbic acid derivative used in the present invention includes one wherein $R^1$ and $R^2$ represent a hydrogen atom, and $R^3$ and $R^4$ each independently represents a hydrogen atom, —$SO_3H$, —$PO_3H_2$, a glycosyl group, or —$COR^{11}$. Examples of such ascorbic acid derivatives can include ascorbic acid 2-phosphate ester, ascorbic acid 3-phosphate ester, ascorbic acid 2-sulfate ester, ascorbic acid 3-sulfate ester, ascorbic acid 2-glucoside, and the like.

Other kinds of the preferred ascorbic acid derivatives used in the present invention include one wherein $R^1$ is —$COR^{11}$, and $R^2$ to $R^4$ all represent a hydrogen atom. Examples of such ascorbic acid derivatives can include ascorbic acid 6-myristate, ascorbic acid 6-palmitate, ascorbic acid 6-stearate, ascorbic acid 2-myristate, ascorbic acid 2-palmitate, ascorbic acid 2-stearate, ascorbic acid 2,6-dimyristate, ascorbic acid 2,6-dipalmitate and ascorbic acid 2,6-distearate, and the like.

The salts of the ascorbic acid derivatives used in the present invention are not particularly limited, if they are agriculturally and horticulturally acceptable salts. Examples thereof can include alkali metal salts such as sodium salts or potassium salts; and alkali earth metal salts such as calcium salts or magnesium salts, and the like.

The ascorbic acid derivatives and their salts used in the present invention can be obtained by known synthesis methods. For example, —$COR^{11}$ can be introduced to any of $R^1$ to $R^4$ by an esterification of a fatty acid compound with ascorbic acid. —$PO_3H_2$ can be introduced to any of $R^1$ to $R^4$ by the esterification of a phosphoric acid compound with ascorbic acid. —$SO_3H$ can be introduced to any of $R^1$ to $R^4$ by the esterification of a sulfuric acid compound with ascorbic acid. In addition, many of the ascorbic acid derivatives used in the present invention are commercially available, and thus, they can be also used.

In addition, the structures of the ascorbic acid derivatives and their salts can be identified and confirmed by known analysis means such as an IR spectrum, NMR spectrum, mass spectrum or elemental analysis. In addition, when a mixture of the ascorbic acid derivative and the salt has been obtained by the above synthesis method, the desired material can be isolated by a known purification method such as extraction, distillation or chromatography.

The anti-plant virus agent of the present invention may contain a compound selected from the group consisting of the aforementioned ascorbic acid derivatives and the salts thereof as an active component, alone or in a combination of two or more thereof.

In addition, the anti-plant virus agent of the present invention may contain other optional components unless an anti-plant viral activity is inhibited by them. Examples of the other optional components can include fillers, extenders, binders, moisturizers, disintegrating agents, lubricants, diluents, excipients, spreading agents, microbicides, fungicides, bactericides, miticides, insecticides, herbicides, growth regulators, solvents, and the like.

In view of the fact that better anti-plant virus agents are obtained, it is preferable that the anti-plant virus agent of the present invention contain a substance which promotes the general resistance of plants against viruses. Examples of the substance promoting such resistance can include microbicides such as probenazole or tiadinil; isonicotinic acid; and salicylic acid, and the like.

In addition, it is preferable that the anti-plant virus agent of the present invention contains a surfactant, so that the ascorbic acid derivatives and the salts thereof can be uniformly dispersed and dissolved in a solvent. Examples of the surfactant can include anionic surfactants, cationic surfactants, nonionic surfactants, amphoteric surfactants, and the like.

The dosage form of the anti-plant virus agent of the present invention is not particularly limited. Depending on the plants to be applied, the dosage form can be appropriately selected from wettable powders, emulsions, water soluble powders, granules, dusts and tablets, and the like. The method for the preparation of the anti-plant virus agent of the present invention is not particularly limited, and can be appropriately selected from the known preparation methods depending on the dosage form.

The application method of the anti-plant virus agent of the present invention is not particularly limited, and can be appropriately determined depending on the nature of each contained component, or the kinds of the plants to be treated, and the like. Preferred examples thereof can include the usage methods by foliage application, dipping treatment, soil irrigation, seed disinfection or smoking, and the like. The anti-plant virus agent of the present invention can be used without being restricted by the type of cultivation such as soil cultivation or hydroponic cultivation. In addition, the agent of the present invention can exhibit an excellent effect even when it is used under a special environment such as a growing point culture.

The application amount of the anti-plant virus agent of the present invention can be appropriately determined depending on weather conditions, the type of formulation, the application period, the application method, the application place, the diseases to be controlled, or the crops to be treated, and the like.

The plants to which the anti-plant virus agent of the present invention can be applied are not particularly limited, and may be either edible plants or non-edible plants. Preferred examples thereof can include woody plants such as cherries or grapes; herbaceous plants such as tobacco or clover; grains such as corn or potatoes; vegetables such as strawberries or radishes; beans such as soybeans or azuki beans; flowering plants such as carnations or roses; and ornamental plants such as daphne.

The plant viruses to be targeted by the anti-plant virus agent of the present invention are not particularly limited. Preferred examples thereof can include geminiviruses having single-stranded DNA genomes, cauliflower mosaic virus having double-stranded DNA genomes, tobacco mosaic virus and tomato bushy stunt virus having single-stranded RNA genomes, and rice ragged stunt virus having double-stranded RNA genomes, and the like.

EXAMPLES

Hereinafter, while the present invention will be more specifically illustrated by way of examples, the scope of the present invention should not be construed as being limited thereto.

(Examples of the Ascorbic Acid Derivatives Used in the Anti-Plant Virus Agent of the Present Invention)

Examples of the ascorbic acid derivatives and the salts thereof, which have been synthesized by the esterification or glycosylation of ascorbic acid, or which are commercially available, are shown in Table 1-1 to Table 1-13. $R^1$ to $R^4$ in the tables correspond to $R^1$ to $R^4$ in Formula (I).

TABLE 1-1

| | $R^1$ | $R^2$ | $R^3$ | $R^4$ |
|---|---|---|---|---|
| 1 | $SO_3H$ | H | H | H |
| 2 | $PO_3H_2$ | H | H | H |
| 3 | glucosyl | H | H | H |
| 4 | mannosyl | H | H | H |
| 5 | galactosyl | H | H | H |
| 6 | $COCH_3$ | H | H | H |
| 7 | $COC_3H_7$-i | H | H | H |
| 8 | $COC_{17}H_{35}$-n | H | H | H |
| 9 | $COC_{16}H_{33}$-n | H | H | H |
| 10 | $COC_{18}H_{37}$-n | H | H | H |
| 11 | $CO(CH_2)_7CH{=}CHC_6H_{13}$-n | H | H | H |
| 12 | $COCH{=}CH_2$ | H | H | H |
| 13 | $COCH_2CH{=}CH_2$ | H | H | H |
| 14 | H | $SO_3H$ | H | H |
| 15 | H | $PO_3H_2$ | H | H |
| 16 | H | glucosyl | H | H |
| 17 | H | mannosyl | H | H |
| 18 | H | galactosyl | H | H |
| 19 | H | $COCH_3$ | H | H |
| 20 | H | $COC_3H_7$-i | H | H |
| 21 | H | $COC_{17}H_{35}$-n | H | H |
| 22 | H | $COC_{16}H_{33}$-n | H | H |
| 23 | H | $COC_{18}H_{37}$-n | H | H |
| 24 | H | $CO(CH_2)_7CH{=}CHC_6H_{13}$-n | H | H |
| 25 | H | $COCH{=}CH_2$ | H | H |
| 26 | H | $COCH_2CH{=}CH_2$ | H | H |
| 27 | H | H | $SO_3H$ | H |
| 28 | H | H | $PO_3H_2$ | H |
| 29 | H | H | glucosyl | H |
| 30 | H | H | mannosyl | H |

TABLE 1-1-continued

| | $R^1$ | $R^2$ | $R^3$ | $R^4$ |
|---|---|---|---|---|
| 31 | H | H | galactosyl | H |
| 32 | H | H | $COCH_3$ | H |
| 33 | H | H | $COC_3H_7$-i | H |
| 34 | H | H | $COC_{17}H_{35}$-n | H |
| 35 | H | H | $COC_{16}H_{33}$-n | H |

TABLE 1-2

| | $R^1$ | $R^2$ | $R^3$ | $R^4$ |
|---|---|---|---|---|
| 36 | H | H | $COC_{18}H_{37}$-n | H |
| 37 | H | H | $CO(CH_2)_7CH{=}CHC_6H_{13}$-n | H |
| 38 | H | H | $COCH{=}CH_2$ | H |
| 39 | H | H | $COCH_2CH{=}CH_2$ | H |
| 40 | H | H | H | $SO_3H$ |
| 41 | H | H | H | $PO_3H_2$ |
| 42 | H | H | H | glucosyl |
| 43 | H | H | H | mannosyl |
| 44 | H | H | H | galactosyl |
| 45 | H | H | H | $COCH_3$ |
| 46 | H | H | H | $COC_3H_7$-i |
| 47 | H | H | H | $COC_{17}H_{35}$-n |
| 48 | H | H | H | $COC_{16}H_{33}$-n |
| 49 | H | H | H | $COC_{18}H_{37}$-n |
| 50 | H | H | H | $CO(CH_2)_7CH{=}CHC_6H_{13}$-n |
| 51 | H | H | H | $COCH{=}CH_2$ |
| 52 | H | H | H | $COCH_2CH{=}CH_2$ |
| 53 | $SO_3H$ | $SO_3H$ | H | H |
| 54 | $SO_3H$ | $PO_3H_2$ | H | H |
| 55 | $SO_3H$ | glucosyl | H | H |
| 56 | $SO_3H$ | mannosyl | H | H |
| 57 | $SO_3H$ | galactosyl | H | H |
| 58 | $SO_3H$ | $COCH_3$ | H | H |
| 59 | $SO_3H$ | $COC_3H_7$-i | H | H |
| 60 | $SO_3H$ | $COC_{17}H_{35}$-n | H | H |
| 61 | $SO_3H$ | $COC_{16}H_{33}$-n | H | H |
| 62 | $SO_3H$ | $COC_{18}H_{37}$-n | H | H |
| 63 | $SO_3H$ | $CO(CH_2)_7CH{=}CHC_6H_{13}$-n | H | H |
| 64 | $SO_3H$ | $COCH{=}CH_2$ | H | H |
| 65 | $SO_3H$ | $COCH_2CH{=}CH_2$ | H | H |
| 66 | $PO_3H_2$ | $SO_3H$ | H | H |
| 67 | $PO_3H_2$ | $PO_3H_2$ | H | H |
| 68 | $PO_3H_2$ | glucosyl | H | H |
| 69 | $PO_3H_2$ | mannosyl | H | H |
| 70 | $PO_3H_2$ | galactosyl | H | H |

TABLE 1-3

| | $R^1$ | $R^2$ | $R^3$ | $R^4$ |
|---|---|---|---|---|
| 71 | $PO_3H_2$ | $COCH_3$ | H | H |
| 72 | $PO_3H_2$ | $COC_3H_7$-i | H | H |
| 73 | $PO_3H_2$ | $COC_{17}H_{35}$-n | H | H |
| 74 | $PO_3H_2$ | $COC_{16}H_{33}$-n | H | H |
| 75 | $PO_3H_2$ | $COC_{18}H_{37}$-n | H | H |
| 76 | $PO_3H_2$ | $CO(CH_2)_7CH{=}CHC_6H_{13}$-n | H | H |
| 77 | $PO_3H_2$ | $COCH{=}CH_2$ | H | H |
| 78 | $PO_3H_2$ | $COCH_2CH{=}CH_2$ | H | H |
| 79 | glucosyl | $SO_3H$ | H | H |
| 80 | glucosyl | $PO_3H_2$ | H | H |
| 81 | glucosyl | glucosyl | H | H |
| 82 | glucosyl | mannosyl | H | H |
| 83 | glucosyl | galactosyl | H | H |
| 84 | glucosyl | $COCH_3$ | H | H |
| 85 | glucosyl | $COC_3H_7$-i | H | H |
| 86 | glucosyl | $COC_{17}H_{35}$-n | H | H |
| 87 | glucosyl | $COC_{16}H_{33}$-n | H | H |
| 88 | glucosyl | $COC_{18}H_{37}$-n | H | H |
| 89 | glucosyl | $CO(CH_2)_7CH{=}CHC_6H_{13}$-n | H | H |
| 90 | glucosyl | $COCH{=}CH_2$ | H | H |
| 91 | glucosyl | $COCH_2CH{=}CH_2$ | H | H |

TABLE 1-3-continued

| | $R^1$ | $R^2$ | $R^3$ | $R^4$ |
|---|---|---|---|---|
| 92 | $COC_{16}H_{33}$-n | $SO_3H$ | H | H |
| 93 | $COC_{16}H_{33}$-n | $PO_3H_2$ | H | H |
| 94 | $COC_{16}H_{33}$-n | glucosyl | H | H |
| 95 | $COC_{16}H_{33}$-n | mannosyl | H | H |
| 96 | $COC_{16}H_{33}$-n | galactosyl | H | H |
| 97 | $COC_{16}H_{33}$-n | $COCH_3$ | H | H |
| 98 | $COC_{16}H_{33}$-n | $COC_3H_7$-i | H | H |
| 99 | $COC_{16}H_{33}$-n | $COC_{17}H_{35}$-n | H | H |
| 100 | $COC_{16}H_{33}$-n | $COC_{16}H_{33}$-n | H | H |
| 101 | $COC_{16}H_{33}$-n | $COC_{18}H_{37}$-n | H | H |
| 102 | $COC_{16}H_{33}$-n | $CO(CH_2)_7CH{=}CHC_6H_{13}$-n | H | H |
| 103 | $COC_{16}H_{33}$-n | $COCH{=}CH_2$ | H | H |
| 104 | $COC_{16}H_{33}$-n | $COCH_2CH{=}CH_2$ | H | H |
| 105 | $CO(CH_2)_7CH{=}CHC_6H_{13}$-n | $SO_3H$ | H | H |

TABLE 1-4

| | $R^1$ | $R^2$ | $R^3$ | $R^4$ |
|---|---|---|---|---|
| 106 | $CO(CH_2)_7CH{=}CHC_6H_{13}$-n | $PO_3H_2$ | H | H |
| 107 | $CO(CH_2)_7CH{=}CHC_6H_{13}$-n | glucosyl | H | H |
| 108 | $CO(CH_2)_7CH{=}CHC_6H_{13}$-n | mannosyl | H | H |
| 109 | $CO(CH_2)_7CH{=}CHC_6H_{13}$-n | galactosyl | H | H |
| 110 | $CO(CH_2)_7CH{=}CHC_6H_{13}$-n | $COCH_3$ | H | H |
| 111 | $CO(CH_2)_7CH{=}CHC_6H_{13}$-n | $COC_3H_7$-i | H | H |
| 112 | $CO(CH_2)_7CH{=}CHC_6H_{13}$-n | $COC_{17}H_{35}$-n | H | H |
| 113 | $CO(CH_2)_7CH{=}CHC_6H_{13}$-n | $COC_{16}H_{33}$-n | H | H |
| 114 | $CO(CH_2)_7CH{=}CHC_6H_{13}$-n | $COC_{18}H_{37}$-n | H | H |
| 115 | $CO(CH_2)_7CH{=}CHC_6H_{13}$-n | $CO(CH_2)_7CH{=}CHC_6H_{13}$-n | H | H |
| 116 | $CO(CH_2)_7CH{=}CHC_6H_{13}$-n | $COCH{=}CH_2$ | H | H |
| 117 | $CO(CH_2)_7CH{=}CHC_6H_{13}$-n | $COCH_2CH{=}CH_2$ | H | H |
| 118 | $SO_3H$ | H | $SO_3H$ | H |
| 119 | $SO_3H$ | H | $PO_3H_2$ | H |
| 120 | $SO_3H$ | H | glucosyl | H |
| 121 | $SO_3H$ | H | mannosyl | H |
| 122 | $SO_3H$ | H | galactosyl | H |
| 123 | $SO_3H$ | H | $COCH_3$ | H |
| 124 | $SO_3H$ | H | $COC_3H_7$-i | H |
| 125 | $SO_3H$ | H | $COC_{17}H_{35}$-n | H |
| 126 | $SO_3H$ | H | $COC_{16}H_{33}$-n | H |
| 127 | $SO_3H$ | H | $COC_{18}H_{37}$-n | H |
| 128 | $SO_3H$ | H | $CO(CH_2)_7CH{=}CHC_6H_{13}$-n | H |
| 129 | $SO_3H$ | H | $COCH{=}CH_2$ | H |
| 130 | $SO_3H$ | H | $COCH_2CH{=}CH_2$ | H |
| 131 | $PO_3H_2$ | H | $SO_3H$ | H |
| 132 | $PO_3H_2$ | H | $PO_3H_2$ | H |
| 133 | $PO_3H_2$ | H | glucosyl | H |
| 134 | $PO_3H_2$ | H | mannosyl | H |
| 135 | $PO_3H_2$ | H | galactosyl | H |
| 136 | $PO_3H_2$ | H | $COCH_3$ | H |
| 137 | $PO_3H_2$ | H | $COC_3H_7$-i | H |
| 138 | $PO_3H_2$ | H | $COC_{17}H_{35}$-n | H |
| 139 | $PO_3H_2$ | H | $COC_{16}H_{33}$-n | H |
| 140 | $PO_3H_2$ | H | $COC_{18}H_{37}$-H | H |

TABLE 1-5

| | $R^1$ | $R^2$ | $R^3$ | $R^4$ |
|---|---|---|---|---|
| 141 | $PO_3H_2$ | H | $CO(CH_2)_7CH{=}CHC_6H_{13}$-n | H |
| 142 | $PO_3H_2$ | H | $COCH{=}CH_2$ | H |
| 143 | $PO_3H_2$ | H | $COCH_2CH{=}CH_2$ | H |
| 144 | glucosyl | H | $SO_3H$ | H |
| 145 | glucosyl | H | $PO_3H_2$ | H |
| 146 | glucosyl | H | glucosyl | H |
| 147 | glucosyl | H | mannosyl | H |
| 148 | glucosyl | H | galactosyl | H |
| 149 | glucosyl | H | $COCH_3$ | H |
| 150 | glucosyl | H | $COC_3H_7$-i | H |
| 151 | glucosyl | H | $COC_{17}H_{35}$-n | H |
| 152 | glucosyl | H | $COC_{16}H_{33}$-n | H |
| 153 | glucosyl | H | $COC_{18}H_{37}$-n | H |
| 154 | glucosyl | H | $CO(CH_2)_7CH{=}CHC_6H_{13}$-n | H |
| 155 | glucosyl | H | $COCH{=}CH_2$ | H |
| 156 | glucosyl | H | $COCH_2CH{=}CH_2$ | H |
| 157 | $COC_{16}H_{33}$-n | H | $SO_3H$ | H |
| 158 | $COC_{16}H_{33}$-n | H | $PO_3H_2$ | H |

TABLE 1-5-continued

| | $R^1$ | $R^2$ | $R^3$ | $R^4$ |
|---|---|---|---|---|
| 159 | $COC_{16}H_{33}$-n | H | glucosyl | H |
| 160 | $COC_{16}H_{33}$-n | H | mannosyl | H |
| 161 | $COC_{16}H_{33}$-n | H | galactosyl | H |
| 162 | $COC_{16}H_{33}$-n | H | $COCH_3$ | H |
| 163 | $COC_{16}H_{33}$-n | H | $COC_3H_7$-i | H |
| 164 | $COC_{16}H_{33}$-n | H | $COC_{17}H_{35}$-n | H |
| 165 | $COC_{16}H_{33}$-n | H | $COC_{16}H_{33}$-n | H |
| 166 | $COC_{16}H_{33}$-n | H | $COC_{18}H_{37}$-n | H |
| 167 | $COC_{16}H_{33}$-n | H | $CO(CH_2)_7CH{=}CHC_6H_{13}$-n | H |
| 168 | $COC_{16}H_{33}$-n | H | $COCH{=}CH_2$ | H |
| 169 | $COC_{16}H_{33}$-n | H | $COCH_2CH{=}CH_2$ | H |
| 170 | $CO(CH_2)_7CH{=}CHC_6H_{13}$-n | H | $SO_3H$ | H |
| 171 | $CO(CH_2)_7CH{=}CHC_6H_{13}$-n | H | $PO_3H_2$ | H |
| 172 | $CO(CH_2)_7CH{=}CHC_6H_{13}$-n | H | glucosyl | H |
| 173 | $CO(CH_2)_7CH{=}CHC_6H_{13}$-n | H | mannosyl | H |
| 174 | $CO(CH_2)_7CH{=}CHC_6H_{13}$-n | H | galactosyl | H |
| 175 | $CO(CH_2)_7CH{=}CHC_6H_{13}$-n | H | $COCH_3$ | H |

TABLE 1-6

| | $R^1$ | $R^2$ | $R^3$ | $R^4$ |
|---|---|---|---|---|
| 176 | $CO(CH_2)_7CH{=}CHC_6H_{13}$-n | H | $COC_3H_7$-i | H |
| 177 | $CO(CH_2)_7CH{=}CHC_6H_{13}$-n | H | $COC_{17}H_{35}$-n | H |
| 178 | $CO(CH_2)_7CH{=}CHC_6H_{13}$-n | H | $COC_{16}H_{33}$-n | H |
| 179 | $CO(CH_2)_7CH{=}CHC_6H_{13}$-n | H | $COC_{18}H_{37}$-n | H |
| 180 | $CO(CH_2)_7CH{=}CHC_6H_{13}$-n | H | $CO(CH_2)_7CH{=}CHC_6H_{13}$-n | H |
| 181 | $CO(CH_2)_7CH{=}CHC_6H_{13}$-n | H | $COCH{=}CH_2$ | H |
| 182 | $CO(CH_2)_7CH{=}CHC_6H_{13}$-n | H | $COCH_2CH{=}CH_2$ | H |
| 183 | $SO_3H$ | H | H | $SO_3H$ |
| 184 | $SO_3H$ | H | H | $PO_3H_2$ |
| 185 | $SO_3H$ | H | H | glucosyl |
| 186 | $SO_3H$ | H | H | mannosyl |

TABLE 1-6-continued

| | $R^1$ | $R^2$ | $R^3$ | $R^4$ |
|---|---|---|---|---|
| 187 | $SO_3H$ | H | H | galactosyl |
| 188 | $SO_3H$ | H | H | $COCH_3$ |
| 189 | $SO_3H$ | H | H | $COC_3H_7$-i |
| 190 | $SO_3H$ | H | H | $COC_{17}H_{35}$-n |
| 191 | $SO_3H$ | H | H | $COC_{16}H_{33}$-n |
| 192 | $SO_3H$ | H | H | $COC_{18}H_{37}$-n |
| 193 | $SO_3H$ | H | H | $CO(CH_2)_7CH{=}CHC_6H_{13}$-n |
| 194 | $SO_3H$ | H | H | $COCH{=}CH_2$ |
| 195 | $SO_3H$ | H | H | $COCH_2CH{=}CH_2$ |
| 196 | $PO_3H_2$ | H | H | $SO_3H$ |
| 197 | $PO_3H_2$ | H | H | $PO_3H_2$ |
| 198 | $PO_3H_2$ | H | H | glucosyl |
| 199 | $PO_3H_2$ | H | H | mannosyl |
| 200 | $PO_3H_2$ | H | H | galactosyl |
| 201 | $PO_3H_2$ | H | H | $COCH_3$ |
| 202 | $PO_3H_2$ | H | H | $COC_3H_7$-i |
| 203 | $PO_3H_2$ | H | H | $COC_{17}H_{35}$-n |
| 204 | $PO_3H_2$ | H | H | $COC_{16}H_{33}$-n |
| 205 | $PO_3H_2$ | H | H | $COC_{18}H_{37}$-n |
| 206 | $PO_3H_2$ | H | H | $CO(CH_2)_7CH{=}CHC_6H_{13}$-n |
| 207 | $PO_3H_2$ | H | H | $COCH{=}CH_2$ |
| 208 | $PO_3H_2$ | H | H | $COCH_2CH{=}CH_2$ |
| 209 | glucosyl | H | H | $SO_3H$ |
| 210 | glucosyl | H | H | $PO_3H_2$ |

TABLE 1-7

| | $R^1$ | $R^2$ | $R^3$ | $R^4$ |
|---|---|---|---|---|
| 211 | glucosyl | H | H | glucosyl |
| 212 | glucosyl | H | H | mannosyl |
| 213 | glucosyl | H | H | galactosyl |
| 214 | glucosyl | H | H | $COCH_3$ |
| 215 | glucosyl | H | H | $COC_3H_7$-i |
| 216 | glucosyl | H | H | $COC_{17}H_{35}$-n |
| 217 | glucosyl | H | H | $COC_{16}H_{33}$-n |
| 218 | glucosyl | H | H | $COC_{18}H_{37}$-n |
| 219 | glucosyl | H | H | $CO(CH_2)_7CH{=}CHC_6H_{13}$-n |
| 220 | glucosyl | H | H | $COCH{=}CH_2$ |
| 221 | glucosyl | H | H | $COCH_2CH{=}CH_2$ |
| 222 | $COC_{16}H_{33}$-n | H | H | $SO_3H$ |
| 223 | $COC_{16}H_{33}$-n | H | H | $PO_3H_2$ |
| 224 | $COC_{16}H_{33}$-n | H | H | glucosyl |
| 225 | $COC_{16}H_{33}$-n | H | H | mannosyl |
| 226 | $COC_{16}H_{33}$-n | H | H | galactosyl |
| 227 | $COC_{16}H_{33}$-n | H | H | $COCH_3$ |
| 228 | $COC_{16}H_{33}$-n | H | H | $COC_3H_7$-i |

TABLE 1-7-continued

| | $R^1$ | $R^2$ | $R^3$ | $R^4$ |
|---|---|---|---|---|
| 229 | $COC_{16}H_{33}$-n | H | H | $COC_{17}H_{35}$-n |
| 230 | $COC_{16}H_{33}$-n | H | H | $COC_{16}H_{33}$-n |
| 231 | $COC_{16}H_{33}$-n | H | H | $COC_{18}H_{37}$-n |
| 232 | $COC_{16}H_{33}$-n | H | H | $CO(CH_2)_7CH{=}CHC_6H_{13}$-n |
| 233 | $COC_{16}H_{33}$-n | H | H | $COCH{=}CH_2$ |
| 234 | $COC_{16}H_{33}$-n | H | H | $COCH_2CH{=}CH_2$ |
| 235 | $CO(CH_2)_7CH{=}CHC_6H_{13}$-n | H | H | $SO_3H$ |
| 236 | $CO(CH_2)_7CH{=}CHC_6H_{13}$-n | H | H | $PO_3H_2$ |
| 237 | $CO(CH_2)_7CH{=}CHC_6H_{13}$-n | H | H | glucosyl |
| 238 | $CO(CH_2)_7CH{=}CHC_6H_{13}$-n | H | H | mannosyl |
| 239 | $CO(CH_2)_7CH{=}CHC_6H_{13}$-n | H | H | galactosyl |
| 240 | $CO(CH_2)_7CH{=}CHC_6H_{13}$-n | H | H | $COCH_3$ |
| 241 | $CO(CH_2)_7CH{=}CHC_6H_{13}$-n | H | H | $COC_3H_7$-i |
| 242 | $CO(CH_2)_7CH{=}CHC_6H_{13}$-n | H | H | $COC_{17}H_{35}$-n |
| 243 | $CO(CH_2)_7CH{=}CHC_6H_{13}$-n | H | H | $COC_{16}H_{33}$-n |
| 244 | $CO(CH_2)_7CH{=}CHC_6H_{13}$-n | H | H | $COC_{18}H_{37}$-n |
| 245 | $CO(CH_2)_7CH{=}CHC_6H_{13}$-n | H | H | $CO(CH_2)_7CH{=}CHC_6H_{13}$-n |

TABLE 1-8

| | $R^1$ | $R^2$ | $R^3$ | $R^4$ |
|---|---|---|---|---|
| 246 | $CO(CH_2)_7CH{=}CHC_6H_{13}$-n | H | H | $COCH{=}CH_2$ |
| 247 | $CO(CH_2)_7CH{=}CHC_6H_{13}$-n | H | H | $COCH_2CH{=}CH_2$ |
| 248 | $SO_3H$ | $SO_3H$ | $SO_3H$ | H |
| 249 | $SO_3H$ | $SO_3H$ | $PO_3H_2$ | H |
| 250 | $SO_3H$ | $SO_3H$ | glucosyl | H |
| 251 | $SO_3H$ | $SO_3H$ | mannosyl | H |
| 252 | $SO_3H$ | $SO_3H$ | galactosyl | H |
| 253 | $SO_3H$ | $SO_3H$ | $COCH_3$ | H |
| 254 | $SO_3H$ | $SO_3H$ | $COC_3H_7$-i | H |
| 255 | $SO_3H$ | $SO_3H$ | $COC_{17}H_{35}$-n | H |
| 256 | $SO_3H$ | $SO_3H$ | $COC_{16}H_{33}$-n | H |
| 257 | $SO_3H$ | $SO_3H$ | $COC_{18}H_{37}$-n | H |
| 258 | $SO_3H$ | $SO_3H$ | $CO(CH_2)_7CH{=}CHC_6H_{13}$-n | H |
| 259 | $SO_3H$ | $SO_3H$ | $COCH{=}CH_2$ | H |
| 260 | $SO_3H$ | $SO_3H$ | $COCH_2CH{=}CH_2$ | H |
| 261 | $PO_3H_2$ | $PO_3H_2$ | $SO_3H$ | H |
| 262 | $PO_3H_2$ | $PO_3H_2$ | $PO_3H_2$ | H |
| 263 | $PO_3H_2$ | $PO_3H_2$ | glucosyl | H |
| 264 | $PO_3H_2$ | $PO_3H_2$ | mannosyl | H |
| 265 | $PO_3H_2$ | $PO_3H_2$ | galactosyl | H |
| 266 | $PO_3H_2$ | $PO_3H_2$ | $COCH_3$ | H |
| 267 | $PO_3H_2$ | $PO_3H_2$ | $COC_3H_7$-i | H |

TABLE 1-8-continued

| | $R^1$ | $R^2$ | $R^3$ | $R^4$ |
|---|---|---|---|---|
| 268 | $PO_3H_2$ | $PO_3H_2$ | $COC_{17}H_{35}$-n | H |
| 269 | $PO_3H_2$ | $PO_3H_2$ | $COC_{16}H_{33}$-n | H |
| 270 | $PO_3H_2$ | $PO_3H_2$ | $COC_{18}H_{37}$-n | H |
| 271 | $PO_3H_2$ | $PO_3H_2$ | $CO(CH_2)_7CH{=}CHC_6H_{13}$-n | H |
| 272 | $PO_3H_2$ | $PO_3H_2$ | $COCH{=}CH_2$ | H |
| 273 | $PO_3H_2$ | $PO_3H_2$ | $COCH_2CH{=}CH_2$ | H |
| 274 | glucosyl | glucosyl | $SO_3H$ | H |
| 275 | glucosyl | glucosyl | $PO_3H_2$ | H |
| 276 | glucosyl | glucosyl | glucosyl | H |
| 277 | glucosyl | glucosyl | mannosyl | H |
| 278 | glucosyl | glucosyl | galactosyl | H |
| 279 | glucosyl | glucosyl | $COCH_3$ | H |
| 280 | glucosyl | glucosyl | $COC_3H_7$-i | H |

TABLE 1-9

| | $R^1$ | $R^2$ | $R^3$ | $R^4$ |
|---|---|---|---|---|
| 281 | glucosyl | glucosyl | $COC_{17}H_{35}$-n | H |
| 282 | glucosyl | glucosyl | $COC_{16}H_{33}$-n | H |
| 283 | glucosyl | glucosyl | $COC_{18}H_{37}$-n | H |
| 284 | glucosyl | glucosyl | $CO(CH_2)_7CH{=}CHC_6H_{13}$-n | H |
| 285 | glucosyl | glucosyl | $COCH{=}CH_2$ | H |
| 286 | glucosyl | glucosyl | $COCH_2CH{=}CH_2$ | H |
| 287 | $COC_{16}H_{33}$-n | $COC_{16}H_{33}$-n | $SO_3H$ | H |
| 288 | $COC_{16}H_{33}$-n | $COC_{16}H_{33}$-n | $PO_3H_2$ | H |
| 289 | $COC_{16}H_{33}$-n | $COC_{16}H_{33}$-n | glucosyl | H |
| 290 | $COC_{16}H_{33}$-n | $COC_{16}H_{33}$-n | mannosyl | H |
| 291 | $COC_{16}H_{33}$-n | $COC_{16}H_{33}$-n | galactosyl | H |
| 292 | $COC_{16}H_{33}$-n | $COC_{16}H_{33}$-n | $COCH_3$ | H |
| 293 | $COC_{16}H_{33}$-n | $COC_{16}H_{33}$-n | $COC_3H_7$-i | H |
| 294 | $COC_{16}H_{33}$-n | $COC_{16}H_{33}$-n | $COC_{17}H_{35}$-n | H |
| 295 | $COC_{16}H_{33}$-n | $COC_{16}H_{33}$-n | $COC_{16}H_{33}$-n | H |
| 296 | $COC_{16}H_{33}$-n | $COC_{16}H_{33}$-n | $COC_{18}H_{37}$-n | H |
| 297 | $COC_{16}H_{33}$-n | $COC_{16}H_{33}$-n | $CO(CH_2)_7CH{=}CHC_6H_{13}$-n | H |
| 298 | $COC_{16}H_{33}$-n | $COC_{16}H_{33}$-n | $COCH{=}CH_2$ | H |
| 299 | $COC_{16}H_{33}$-n | $COC_{16}H_{33}$-n | $COCH_2CH{=}CH_2$ | H |
| 300 | $CO(CH_2)_7CH{=}CHC_6H_{13}$-n | $CO(CH_2)_7CH{=}CHC_6H_{13}$-n | $SO_3H$ | H |
| 301 | $CO(CH_2)_7CH{=}CHC_6H_{13}$-n | $CO(CH_2)_7CH{=}CHC_6H_{13}$-n | $PO_3H_2$ | H |
| 302 | $CO(CH_2)_7CH{=}CHC_6H_{13}$-n | $CO(CH_2)_7CH{=}CHC_6H_{13}$-n | glucosyl | H |
| 303 | $CO(CH_2)_7CH{=}CHC_6H_{13}$-n | $CO(CH_2)_7CH{=}CHC_6H_{13}$-n | mannosyl | H |
| 304 | $CO(CH_2)_7CH{=}CHC_6H_{13}$-n | $CO(CH_2)_7CH{=}CHC_6H_{13}$-n | galactosyl | H |
| 305 | $CO(CH_2)_7CH{=}CHC_6H_{13}$-n | $CO(CH_2)_7CH{=}CHC_6H_{13}$-n | $COCH_3$ | H |
| 306 | $CO(CH_2)_7CH{=}CHC_6H_{13}$-n | $CO(CH_2)_7CH{=}CHC_6H_{13}$-n | $COC_3H_7$-i | H |
| 307 | $CO(CH_2)_7CH{=}CHC_6H_{13}$-n | $CO(CH_2)_7CH{=}CHC_6H_{13}$-n | $COC_{17}H_{35}$-n | H |
| 308 | $CO(CH_2)_7CH{=}CHC_6H_{13}$-n | $CO(CH_2)_7CH{=}CHC_6H_{13}$-n | $COC_{16}H_{33}$-n | H |
| 309 | $CO(CH_2)_7CH{=}CHC_6H_{13}$-n | $CO(CH_2)_7CH{=}CHC_6H_{13}$-n | $COC_{18}H_{37}$-n | H |
| 310 | $CO(CH_2)_7CH{=}CHC_6H_{13}$-n | $CO(CH_2)_7CH{=}CHC_6H_{13}$-n | $CO(CH_2)_7CH{=}CHC_6H_{13}$-n | H |
| 311 | $CO(CH_2)_7CH{=}CHC_6H_{13}$-n | $CO(CH_2)_7CH{=}CHC_6H_{13}$-n | $COCH{=}CH_2$ | H |
| 312 | $CO(CH_2)_7CH{=}CHC_6H_{13}$-n | $CO(CH_2)_7CH{=}CHC_6H_{13}$-n | $COCH_2CH{=}CH_2$ | H |
| 313 | $SO_3H$ | $SO_3H$ | H | $SO_3H$ |
| 314 | $SO_3H$ | $SO_3H$ | H | $PO_3H_2$ |
| 315 | $SO_3H$ | $SO_3H$ | H | glucosyl |

TABLE 1-10

| | $R^1$ | $R^2$ | $R^3$ | $R^4$ |
|---|---|---|---|---|
| 316 | $SO_3H$ | $SO_3H$ | H | mannosyl |
| 317 | $SO_3H$ | $SO_3H$ | H | galactosyl |
| 318 | $SO_3H$ | $SO_3H$ | H | $COCH_3$ |
| 319 | $SO_3H$ | $SO_3H$ | H | $COC_3H_7$-i |
| 320 | $SO_3H$ | $SO_3H$ | H | $COC_{17}H_{35}$-n |
| 321 | $SO_3H$ | $SO_3H$ | H | $COC_{16}H_{33}$-n |
| 322 | $SO_3H$ | $SO_3H$ | H | $COC_{18}H_{37}$-n |
| 323 | $SO_3H$ | $SO_3H$ | H | $CO(CH_2)_7CH{=}CHC_6H_{13}$-n |
| 324 | $SO_3H$ | $SO_3H$ | H | $COCH{=}CH_2$ |
| 325 | $SO_3H$ | $SO_3H$ | H | $COCH_2CH{=}CH_2$ |
| 326 | $PO_3H_2$ | $PO_3H_2$ | H | $SO_3H$ |
| 327 | $PO_3H_2$ | $PO_3H_2$ | H | $PO_3H_2$ |
| 328 | $PO_3H_2$ | $PO_3H_2$ | H | glucosyl |

TABLE 1-10-continued

| | $R^1$ | $R^2$ | $R^3$ | $R^4$ |
|---|---|---|---|---|
| 329 | $PO_3H_2$ | $PO_3H_2$ | H | mannosyl |
| 330 | $PO_3H_2$ | $PO_3H_2$ | H | galactosyl |
| 331 | $PO_3H_2$ | $PO_3H_2$ | H | $COCH_3$ |
| 332 | $PO_3H_2$ | $PO_3H_2$ | H | $COC_3H_7$-i |
| 333 | $PO_3H_2$ | $PO_3H_2$ | H | $COC_{17}H_{35}$-n |
| 334 | $PO_3H_2$ | $PO_3H_2$ | H | $COC_{16}H_{33}$-n |
| 335 | $PO_3H_2$ | $PO_3H_2$ | H | $COC_{18}H_{37}$-n |
| 336 | $PO_3H_2$ | $PO_3H_2$ | H | $CO(CH_2)_7CH{=}CHC_6H_{13}$-n |
| 337 | $PO_3H_2$ | $PO_3H_2$ | H | $COCH{=}CH_2$ |
| 338 | $PO_3H_2$ | $PO_3H_2$ | H | $COCH_2CH{=}CH_2$ |
| 339 | glucosyl | glucosyl | H | $SO_3H$ |
| 340 | glucosyl | glucosyl | H | $PO_3H_2$ |
| 341 | glucosyl | glucosyl | H | glucosyl |

TABLE 1-10-continued

| | $R^1$ | $R^2$ | $R^3$ | $R^4$ |
|---|---|---|---|---|
| 342 | glucosyl | glucosyl | H | mannosyl |
| 343 | glucosyl | glucosyl | H | galactosyl |
| 344 | glucosyl | glucosyl | H | $COCH_3$ |
| 345 | glucosyl | glucosyl | H | $COC_3H_7$-i |
| 346 | glucosyl | glucosyl | H | $COC_{17}H_{35}$-n |
| 347 | glucosyl | glucosyl | H | $COC_{16}H_{33}$-n |
| 348 | glucosyl | glucosyl | H | $COC_{18}H_{37}$-n |
| 349 | glucosyl | glucosyl | H | $CO(CH_2)_7CH{=}CHC_6H_{13}$-n |
| 350 | glucosyl | glucosyl | H | $COCH{=}CH_2$ |

TABLE 1-11

| | $R^1$ | $R^2$ | $R^3$ | $R^4$ |
|---|---|---|---|---|
| 351 | glucosyl | glucosyl | H | $COCH_2CH{=}CH_2$ |
| 352 | $COC_{16}H_{33}$-n | $COC_{16}H_{33}$-n | H | $SO_3H$ |
| 353 | $COC_{16}H_{33}$-n | $COC_{16}H_{33}$-n | H | $PO_3H_2$ |
| 354 | $COC_{16}H_{33}$-n | $COC_{16}H_{33}$-n | H | glucosyl |
| 355 | $COC_{16}H_{33}$-n | $COC_{16}H_{33}$-n | H | mannosyl |
| 356 | $COC_{16}H_{33}$-n | $COC_{16}H_{33}$-n | H | galactosyl |
| 357 | $COC_{16}H_{33}$-n | $COC_{16}H_{33}$-n | H | $COCH_3$ |
| 358 | $COC_{16}H_{33}$-n | $COC_{16}H_{33}$-n | H | $COC_3H_7$-i |
| 359 | $COC_{16}H_{33}$-n | $COC_{16}H_{33}$-n | H | $COC_{17}H_{35}$-n |
| 360 | $COC_{16}H_{33}$-n | $COC_{16}H_{33}$-n | H | $COC_{16}H_{33}$-n |
| 361 | $COC_{16}H_{33}$-n | $COC_{16}H_{33}$-n | H | $COC_{18}H_{37}$-n |
| 362 | $COC_{16}H_{33}$-n | $COC_{16}H_{33}$-n | H | $CO(CH_2)_7CH{=}CHC_6H_{13}$-n |
| 363 | $COC_{16}H_{33}$-n | $COC_{16}H_{33}$-n | H | $COCH{=}CH_2$ |
| 364 | $COC_{16}H_{33}$-n | $COC_{16}H_{33}$-n | H | $COCH_2CH{=}CH_2$ |
| 365 | $CO(CH_2)_7CH{=}CHC_6H_{13}$-n | $CO(CH_2)_7CH{=}CHC_6H_{13}$-n | H | $SO_3H$ |
| 366 | $CO(CH_2)_7CH{=}CHC_6H_{13}$-n | $CO(CH_2)_7CH{=}CHC_6H_{13}$-n | H | $PO_3H_2$ |
| 367 | $CO(CH_2)_7CH{=}CHC_6H_{13}$-n | $CO(CH_2)_7CH{=}CHC_6H_{13}$-n | H | glucosyl |
| 368 | $CO(CH_2)_7CH{=}CHC_6H_{13}$-n | $CO(CH_2)_7CH{=}CHC_6H_{13}$-n | H | mannosyl |
| 369 | $CO(CH_2)_7CH{=}CHC_6H_{13}$-n | $CO(CH_2)_7CH{=}CHC_6H_{13}$-n | H | galactosyl |
| 370 | $CO(CH_2)_7CH{=}CHC_6H_{13}$-n | $CO(CH_2)_7CH{=}CHC_6H_{13}$-n | H | $COCH_3$ |
| 371 | $CO(CH_2)_7CH{=}CHC_6H_{13}$-n | $CO(CH_2)_7CH{=}CHC_6H_{13}$-n | H | $COC_3H_7$-i |
| 372 | $CO(CH_2)_7CH{=}CHC_6H_{13}$-n | $CO(CH_2)_7CH{=}CHC_6H_{13}$-n | H | $COC_{17}H_{35}$-n |
| 373 | $CO(CH_2)_7CH{=}CHC_6H_{13}$-n | $CO(CH_2)_7CH{=}CHC_6H_{13}$-n | H | $COC_{16}H_{33}$-n |
| 374 | $CO(CH_2)_7CH{=}CHC_6H_{13}$-n | $CO(CH_2)_7CH{=}CHC_6H_{13}$-n | H | $COC_{18}H_{37}$-n |
| 375 | $CO(CH_2)_7CH{=}CHC_6H_{13}$-n | $CO(CH_2)_7CH{=}CHC_6H_{13}$-n | H | $CO(CH_2)_7CH{=}CHC_6H_{13}$-n |
| 376 | $CO(CH_2)_7CH{=}CHC_6H_{13}$-n | $CO(CH_2)_7CH{=}CHC_6H_{13}$-n | H | $COCH{=}CH_2$ |
| 377 | $CO(CH_2)_7CH{=}CHC_6H_{13}$-n | $CO(CH_2)_7CH{=}CHC_6H_{13}$-n | H | $COCH_2CH{=}CH_2$ |
| 378 | $SO_3H$ | $SO_3H$ | $SO_3H$ | $SO_3H$ |
| 379 | $SO_3H$ | $SO_3H$ | $SO_3H$ | $PO_3H_2$ |
| 380 | $SO_3H$ | $SO_3H$ | $SO_3H$ | glucosyl |
| 381 | $SO_3H$ | $SO_3H$ | $SO_3H$ | mannosyl |
| 382 | $SO_3H$ | $SO_3H$ | $SO_3H$ | galactosyl |
| 383 | $SO_3H$ | $SO_3H$ | $SO_3H$ | $COCH_3$ |
| 384 | $SO_3H$ | $SO_3H$ | $SO_3H$ | $COC_3H_7$-i |
| 385 | $SO_3H$ | $SO_3H$ | $SO_3H$ | $COC_{17}H_{35}$-n |

TABLE 1-12

| | $R^1$ | $R^2$ | $R^3$ | $R^4$ |
|---|---|---|---|---|
| 386 | $SO_3H$ | $SO_3H$ | $SO_3H$ | $COC_{16}H_{33}$-n |
| 387 | $SO_3H$ | $SO_3H$ | $SO_3H$ | $COC_{18}H_{37}$-n |
| 388 | $SO_3H$ | $SO_3H$ | $SO_3H$ | $CO(CH_2)_7CH{=}CHC_6H_{13}$-n |
| 389 | $SO_3H$ | $SO_3H$ | $SO_3H$ | $COCH{=}CH_2$ |
| 390 | $SO_3H$ | $SO_3H$ | $SO_3H$ | $COCH_2CH{=}CH_2$ |
| 391 | $PO_3H_2$ | $PO_3H_2$ | $PO_3H_2$ | $SO_3H$ |
| 392 | $PO_3H_2$ | $PO_3H_2$ | $PO_3H_2$ | $PO_3H_2$ |
| 393 | $PO_3H_2$ | $PO_3H_2$ | $PO_3H_2$ | glucosyl |
| 394 | $PO_3H_2$ | $PO_3H_2$ | $PO_3H_2$ | mannosyl |
| 395 | $PO_3H_2$ | $PO_3H_2$ | $PO_3H_2$ | galactosyl |
| 396 | $PO_3H_2$ | $PO_3H_2$ | $PO_3H_2$ | $COCH_3$ |
| 397 | $PO_3H_2$ | $PO_3H_2$ | $PO_3H_2$ | $COC_3H_7$-i |
| 398 | $PO_3H_2$ | $PO_3H_2$ | $PO_3H_2$ | $COC_{17}H_{35}$-n |
| 399 | $PO_3H_2$ | $PO_3H_2$ | $PO_3H_2$ | $COC_{16}H_{33}$-n |
| 400 | $PO_3H_2$ | $PO_3H_2$ | $PO_3H_2$ | $COC_{18}H_{37}$-n |
| 401 | $PO_3H_2$ | $PO_3H_2$ | $PO_3H_2$ | $CO(CH_2)_7CH{=}CHC_6H_{13}$-n |
| 402 | $PO_3H_2$ | $PO_3H_2$ | $PO_3H_2$ | $COCH{=}CH_2$ |
| 403 | $PO_3H_2$ | $PO_3H_2$ | $PO_3H_2$ | $COCH_2CH{=}CH_2$ |
| 404 | glucosyl | glucosyl | glucosyl | $SO_3H$ |
| 405 | glucosyl | glucosyl | glucosyl | $PO_3H_2$ |
| 406 | glucosyl | glucosyl | glucosyl | glucosyl |
| 407 | glucosyl | glucosyl | glucosyl | mannosyl |

TABLE 1-12-continued

| | $R^1$ | $R^2$ | $R^3$ | $R^4$ |
|---|---|---|---|---|
| 408 | glucosyl | glucosyl | glucosyl | galactosyl |
| 409 | glucosyl | glucosyl | glucosyl | $COCH_3$ |
| 410 | glucosyl | glucosyl | glucosyl | $COC_3H_7$-i |
| 411 | glucosyl | glucosyl | glucosyl | $COC_{17}H_{35}$-n |
| 412 | glucosyl | glucosyl | glucosyl | $COC_{16}H_{33}$-n |
| 413 | glucosyl | glucosyl | glucosyl | $COC_{18}H_{37}$-n |
| 414 | glucosyl | glucosyl | glucosyl | $CO(CH_2)_7CH{=}CHC_6H_{13}$-n |
| 415 | glucosyl | glucosyl | glucosyl | $COCH{=}CH_2$ |
| 416 | glucosyl | glucosyl | glucosyl | $COCH_2CH{=}CH_2$ |
| 417 | $COC_{16}H_{33}$-n | $COC_{16}H_{33}$-n | $COC_{16}H_{33}$-n | $SO_3H$ |
| 418 | $COC_{16}H_{33}$-n | $COC_{16}H_{33}$-n | $COC_{16}H_{33}$-n | $PO_3H_2$ |
| 419 | $COC_{16}H_{33}$-n | $COC_{16}H_{33}$-n | $COC_{16}H_{33}$-n | glucosyl |
| 420 | $COC_{16}H_{33}$-n | $COC_{16}H_{33}$-n | $COC_{16}H_{33}$-n | mannosyl |

TABLE 1-13

| | $R^1$ | $R^2$ | $R^3$ | $R^4$ |
|---|---|---|---|---|
| 421 | $COC_{16}H_{33}$-n | $COC_{16}H_{33}$-n | $COC_{16}H_{33}$-n | galactosyl |
| 422 | $COC_{16}H_{33}$-n | $COC_{16}H_{33}$-n | $COC_{16}H_{33}$-n | $COCH_3$ |
| 423 | $COC_{16}H_{33}$-n | $COC_{16}H_{33}$-n | $COC_{16}H_{33}$-n | $COC_3H_7$-i |
| 424 | $COC_{16}H_{33}$-n | $COC_{16}H_{33}$-n | $COC_{16}H_{33}$-n | $COC_{17}H_{35}$-n |
| 425 | $COC_{16}H_{33}$-n | $COC_{16}H_{33}$-n | $COC_{16}H_{33}$-n | $COC_{16}H_{33}$-n |
| 426 | $COC_{16}H_{33}$-n | $COC_{16}H_{33}$-n | $COC_{16}H_{33}$-n | $COC_{18}H_{37}$-n |
| 427 | $COC_{16}H_{33}$-n | $COC_{16}H_{33}$-n | $COC_{16}H_{33}$-n | $CO(CH_2)_7CH{=}CHC_6H_{13}$-n |
| 428 | $COC_{16}H_{33}$-n | $COC_{16}H_{33}$-n | $COC_{16}H_{33}$-n | $COCH{=}CH_2$ |
| 429 | $COC_{16}H_{33}$-n | $COC_{16}H_{33}$-n | $COC_{16}H_{33}$-n | $COCH_2CH{=}CH_2$ |
| 430 | $CO(CH_2)_7CH{=}CHC_6H_{13}$-n | $CO(CH_2)_7CH{=}CHC_6H_{13}$-n | $CO(CH_2)_7CH{=}CHC_6H_{13}$-n | $SO_3H$ |
| 431 | $CO(CH_2)_7CH{=}CHC_6H_{13}$-n | $CO(CH_2)_7CH{=}CHC_6H_{13}$-n | $CO(CH_2)_7CH{=}CHC_6H_{13}$-n | $PO_3H_2$ |
| 432 | $CO(CH_2)_7CH{=}CHC_6H_{13}$-n | $CO(CH_2)_7CH{=}CHC_6H_{13}$-n | $CO(CH_2)_7CH{=}CHC_6H_{13}$-n | glucosyl |
| 433 | $CO(CH_2)_7CH{=}CHC_6H_{13}$-n | $CO(CH_2)_7CH{=}CHC_6H_{13}$-n | $CO(CH_2)_7CH{=}CHC_6H_{13}$-n | mannosyl |
| 434 | $CO(CH_2)_7CH{=}CHC_6H_{13}$-n | $CO(CH_2)_7CH{=}CHC_6H_{13}$-n | $CO(CH_2)_7CH{=}CHC_6H_{13}$-n | galactosyl |
| 435 | $CO(CH_2)_7CH{=}CHC_6H_{13}$-n | $CO(CH_2)_7CH{=}CHC_6H_{13}$-n | $CO(CH_2)_7CH{=}CHC_6H_{13}$-n | $COCH_3$ |
| 436 | $CO(CH_2)_7CH{=}CHC_6H_{13}$-n | $CO(CH_2)_7CH{=}CHC_6H_{13}$-n | $CO(CH_2)_7CH{=}CHC_6H_{13}$-n | $COC_3H_7$-i |
| 437 | $CO(CH_2)_7CH{=}CHC_6H_{13}$-n | $CO(CH_2)_7CH{=}CHC_6H_{13}$-n | $CO(CH_2)_7CH{=}CHC_6H_{13}$-n | $COC_{17}H_{35}$-n |
| 438 | $CO(CH_2)_7CH{=}CHC_6H_{13}$-n | $CO(CH_2)_7CH{=}CHC_6H_{13}$-n | $CO(CH_2)_7CH{=}CHC_6H_{13}$-n | $COC_{16}H_{33}$-n |
| 439 | $CO(CH_2)_7CH{=}CHC_6H_{13}$-n | $CO(CH_2)_7CH{=}CHC_6H_{13}$-n | $CO(CH_2)_7CH{=}CHC_6H_{13}$-n | $COC_{18}H_{37}$-n |
| 440 | $CO(CH_2)_7CH{=}CHC_6H_{13}$-n | $CO(CH_2)_7CH{=}CHC_6H_{13}$-n | $CO(CH_2)_7CH{=}CHC_6H_{13}$-n | $CO(CH_2)_7CH{=}CHC_6H_{13}$-n |
| 441 | $CO(CH_2)_7CH{=}CHC_6H_{13}$-n | $CO(CH_2)_7CH{=}CHC_6H_{13}$-n | $CO(CH_2)_7CH{=}CHC_6H_{13}$-n | $COCH{=}CH_2$ |
| 442 | $CO(CH_2)_7CH{=}CHC_6H_{13}$-n | $CO(CH_2)_7CH{=}CHC_6H_{13}$-n | $CO(CH_2)_7CH{=}CHC_6H_{13}$-n | $COCH_2CH{=}CH_2$ |

Experiment I

Comparative Example 1

Each of the frozen tobacco leaves infected with Turnip mosaic virus and Cucumber mosaic virus (Y strain) was triturated in 0.1M phosphate-buffer solution at a 10-fold amount (containing 10 mM diethyldithiocarbamic acid (DIECA)). These were defined as virus inoculation solutions A and B. These virus inoculation solutions A and B are solutions causing a 100% incidence.

Three expanded leaves per one column of *Arabidopsis thaliana* (Columbia) were inoculated with each virus via the aforementioned virus inoculation solutions A and B by the carborundum method.

On the $3^{rd}$ day and the $1^{st}$ day prior to the date of the virus inoculation, and on the $1^{st}$ day, the $3^{rd}$ day, the $5^{th}$ day, the $8^{th}$ day and the $10^{th}$ days after the date of the virus inoculation, an aqueous solution of 0.1% of a spreading agent (Approach BI: manufactured by Kao Corporation) was sprayed thereon.

On the $14^{th}$ day after the virus inoculation, the presence or absence of disease symptoms such as yellow mosaic of new leaves, leaf curling, and plant stunting was observed. Each of all seven columns inoculated with Turnip mosaic virus and Cucumber mosaic virus (Y strain) showed symptoms. It can be seen that the above virus inoculation solutions A and B are strong solutions in view of the fact that the inoculation with the solutions reliably causes the onset of symptoms.

Comparative Example 2

Each was dissolved in water so as to be 20 mM ascorbic acid and 0.1% of a spreading agent (Approach BI: manufactured by Kao Corporation), thereby obtaining an aqueous solution of ascorbic acid. Except that the aqueous solution of ascorbic acid was sprayed onto *Arabidopsis thaliana* instead of the aqueous solution of the spreading agent, in the same manner as Comparative Example 1, Turnip mosaic virus and Cucumber mosaic virus (Y strain) were inoculated onto *Arabidopsis thaliana*, and then the onset of symptoms was examined. Each of all seven columns inoculated with Turnip mosaic virus and Cucumber mosaic virus (Y strain) showed symptoms.

Example 1

Ascorbic acid 6-palmitate, a nonionic surfactant (polyoxyethylene sorbitan monolaurate) and a spreading agent (Approach BI: manufactured by Kao Corporation) were dissolved in N,N-dimethylformamide. This solution was added to water to obtain an aqueous solution of the anti-plant virus agent comprising 20 mM ascorbic acid 6-palmitate, 0.05% of a nonionic surfactant, 0.1% of a spreading agent, and 1% of N,N-dimethylformamide. Except that the aqueous solution of the anti-plant virus agent was sprayed thereon instead of the aqueous solution of ascorbic acid, in the same manner as Comparative Example 2, Turnip mosaic virus and Cucumber mosaic virus (Y strain) were inoculated onto *Arabidopsis thaliana*, and then the onset of symptoms was examined. Among each of the seven columns inoculated with Turnip mosaic virus and Cucumber mosaic virus (Y strain), each of five columns showed symptoms, and each of two columns were healthy.

Example 2

Each was added to water so as to be 20 mM ascorbic acid 2-phosphate ester 3-sodium and 0.1% of a spreading agent (Approach BI: manufactured by Kao Corporation), thereby obtaining an aqueous solution of the anti-plant virus agent. Except that the aqueous solution of the anti-plant virus agent was sprayed thereon instead of the aqueous solution of ascorbic acid, in the same manner as Comparative Example 2, Turnip mosaic virus was inoculated onto *Arabidopsis thaliana*, and then the onset of symptoms was examined. Among the seven columns inoculated with Turnip mosaic virus, five columns showed symptoms, and two columns were healthy.

About 28% of the entire *Arabidopsis thaliana* on which the anti-plant virus agent of the present invention was sprayed did not show symptoms and were healthy. On the other hand, for *Arabidopsis thaliana* on which the aqueous solution of ascorbic acid was sprayed, all columns showed symptoms. It can be seen that ascorbic acid does not have any anti-plant viral activity.

Experiment II

Comparative Example 3

The frozen tobacco leaves infected with Turnip mosaic virus were triturated in 0.1M phosphate-buffer solution at a 10-fold amount (containing 10 mM DIECA). Then, this was diluted 50 times with the same buffer solution. This was defined as virus inoculation solution C.

Two expanded leaves per one column of *Arabidopsis thaliana* (Columbia) were inoculated with the virus via the aforementioned virus inoculation solution C by the carborundum method.

On the 3$^{rd}$ day and the 1$^{st}$ day prior to the date of the virus inoculation, an aqueous solution of 0.1% a spreading agent (Approach BI: manufactured by Kao Corporation) was sprayed thereon.

On the 16$^{th}$ day after the date of the virus inoculation, the presence or absence of disease symptoms such as yellow mosaic of new leaves, leaf curling, and plant stunting was observed. Among the ten columns inoculated with Turnip mosaic virus, four columns showed symptoms, and six columns were healthy.

Comparative Example 4

Each was dissolved in water so as to be 20 mM ascorbic acid and 0.1% of a spreading agent (Approach BI: manufactured by Kao Corporation), thereby obtaining an aqueous solution of ascorbic acid. Except that the aqueous solution of ascorbic acid was sprayed onto *Arabidopsis thaliana* instead of the aqueous solution of the spreading agent, in the same manner as Comparative Example 3, Turnip mosaic virus was inoculated onto *Arabidopsis thaliana*, and then the onset of symptoms was examined. Among the ten columns inoculated with Turnip mosaic virus, two columns showed symptoms, and eight columns were healthy.

Comparative Example 5

Except that sodium ascorbate was used instead of ascorbic acid, in the same manner as Comparative Example 4, Turnip mosaic virus was inoculated onto *Arabidopsis thaliana*, and then the onset of symptoms was examined. Among the ten columns inoculated with Turnip mosaic virus, three columns showed symptoms, and seven columns were healthy.

Example 3

Each was added to water so as to be 20 mM ascorbic acid 2-phosphate ester 3-sodium and 0.1% of a spreading agent (Approach BI: manufactured by Kao Corporation), thereby obtaining an aqueous solution of the anti-plant virus agent. Except that the aqueous solution of the anti-plant virus agent was used instead of the aqueous solution of ascorbic acid, in the same manner as Comparative Example 4, Turnip mosaic virus was inoculated onto *Arabidopsis thaliana*, and then the onset of symptoms was examined. All of the ten columns inoculated with Turnip mosaic virus were healthy.

Example 4

Each was added to water so as to be 20 mM ascorbic acid 2-glucoside and 0.1% of a spreading agent (Approach BI: manufactured by Kao Corporation), thereby obtaining an aqueous solution of the anti-plant virus agent. Except that the aqueous solution of the anti-plant virus agent was used instead of the aqueous solution of ascorbic acid, in the same manner as Comparative Example 4, Turnip mosaic virus was inoculated onto *Arabidopsis thaliana*, and then the onset of symptoms was examined. Among the ten columns inoculated with Turnip mosaic virus, one column showed symptoms, and nine columns were healthy.

From the above, it can be seen that the aqueous solution of the anti-plant virus agent of the present invention showed a preventive value of 75% or more, and exhibits preventive effects against plant virus diseases. On the other hand, it can be seen that the ascorbic acid and the salts thereof do not have any anti-plant viral activity.

Experiment III

Comparative Example 6

A nonionic surfactant (polyoxyethylene sorbitan monolaurate) and a spreading agent (Approach BI: manufactured by Kao Corporation) were dissolved in N,N-dimethylformamide. This solution was added to water to obtain an aqueous solution comprising 0.05% of a nonionic surfactant, 0.1% of a spreading agent, and 1% of N,N-dimethylformamide.

Two expanded leaves per one column of *Arabidopsis thaliana* (Columbia) were inoculated with the virus via the aforementioned virus inoculation solution C by the carborundum method.

On the 1$^{st}$ day, the 4$^{th}$ day, the 7$^{th}$ day and the 10$^{th}$ day after the date of the virus inoculation, the aforementioned aqueous solution was sprayed thereon.

On the 16$^{th}$ day after the date of the virus inoculation, the presence or absence of disease symptoms such as yellow mosaic of new leaves, leaf curling, plant stunting was observed. Among the ten columns inoculated with Turnip mosaic virus, three columns showed symptoms, and seven columns were healthy.

Example 5

Ascorbic acid 6-palmitate, a nonionic surfactant (polyoxyethylene sorbitan monolaurate) and a spreading agent (Approach BI: manufactured by Kao Corporation) were dissolved in N,N-dimethylformamide. This solution was added to water to obtain an aqueous solution of the anti-plant virus agent comprising 20 mM ascorbic acid 6-palmitate, 0.05% of a nonionic surfactant, 0.1% of a spreading agent, and 1% of N,N-dimethylformamide.

Except that the aqueous solution of the anti-plant virus agent was sprayed onto *Arabidopsis thaliana* instead of the aforementioned aqueous solution, in the same manner as Comparative Example 6, Turnip mosaic virus was inoculated onto *Arabidopsis thaliana*, and then the onset of the symptoms was examined. Among the ten columns inoculated with Turnip mosaic virus, one column showed symptoms, and nine columns were healthy.

Example 6

Except that ascorbic acid 2,6-dipalmitate was used instead of ascorbic acid 6-palmitate, in the same manner as Example 5, Turnip mosaic virus was inoculated onto *Arabidopsis thaliana*, and then the onset of the symptoms was examined. Among the ten columns inoculated with Turnip mosaic virus, one column showed symptoms, and nine columns were healthy.

Example 7

Except that ascorbic acid 6-stearate was used instead of ascorbic acid 6-palmitate, in the same manner as Example 5, Turnip mosaic virus was inoculated onto *Arabidopsis thaliana*, and then the onset of the symptoms was examined. Among the ten columns inoculated with Turnip mosaic virus, one column showed symptoms, and nine columns were healthy.

Example 8

Except that ascorbyl 2,3,5,6-tetrahexyldecanoate was used instead of ascorbic acid 6-palmitate, in the same manner as Example 5, Turnip mosaic virus was inoculated onto *Arabidopsis thaliana*, and then the onset of the symptoms was examined. Among the ten columns inoculated with Turnip mosaic virus, one column showed symptoms, and nine columns were healthy.

From the above, it can be seen that the anti-plant virus agent of the present invention exhibits therapeutic effects against plant virus diseases.

Experiment IV

Comparative Example 7

The frozen tobacco (*Nicotiana benthamiana*) infected with Tomato aspermy virus (V strain) was triturated in 0.1M phosphate-buffer solution at a 10-fold amount (containing 10 mM DIECA), and was filtered through a double gauze and the filtrate was defined as virus inoculation solution D. Onto fully expanded leaves of the seedling stage of tomato (cultivar: Beiju) after a period of two weeks from seeding, the virus inoculation solution D was inoculated by physical application via the carborundum method.

After the virus inoculation, as a result of examination of disease symptoms over time, mosaic or leaf curling could be recognized after the $5^{th}$ day, and lethal necrosis symptoms were shown after the period of two weeks, and all of the five columns inoculated with Tomato aspermy virus (V strain) withered.

Example 9

200 mM of ascorbic acid 6-palmitate was dissolved in N,N-dimethylformamide. This solution was diluted 100 times with distilled water to obtain an aqueous solution of the anti-plant virus agent comprising 2 mM ascorbic acid 6-palmitate and 1% of N,N-dimethylformamide. In the same manner as Comparative Example 7, the tomato was inoculated with tomato aspermy virus (V strain). During the two weeks from the date of virus inoculation, the aforementioned aqueous solution was sprayed thereon every day, and disease symptoms were examined over time.

On the $30^{th}$ day after the date of the inoculation, the presence or absence of disease symptoms was observed, and as a result, among the four columns inoculated with Tomato aspermy virus (V strain), two columns withered, and two columns were healthy. With regard to the two healthy columns, they showed more vigorous growth compared with the tomato on which the virus had not been inoculated and ascorbic acid 6-palmitate had not been sprayed.

INDUSTRIAL APPLICABILITY

The anti-plant virus agent of the present invention has a high anti-plant viral activity. The application of the anti-plant virus agent of the present invention to normal plants makes it possible to effectively prevent infection by plant viruses (preventive effect). In addition, the application of the anti-plant virus agent of the present invention to plants infected with plant viruses makes it possible to suppress the onset of plant diseases (therapeutic effect). Given the above, the present invention is industrially very useful.

The invention claimed is:

1. A method for controlling a plant virus comprising applying to a plant in need of virus control at least one compound selected from the group consisting of ascorbic acid derivatives represented by Formula I and salts thereof:

(Formula I):

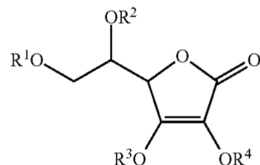

wherein, $R^1$ to $R^4$ each independently represents a hydrogen atom, —$SO_3H$, —$PO_3H_2$, a glycosyl group, or —$COR^{11}$, wherein $R^{11}$ represents an unsubstituted or substituted C1-30 alkyl group, or an unsubstituted or substituted C2-30 alkenyl group; with the proviso that $R^1$ to $R^4$ may not all be hydrogen atoms at the same time, wherein the application of the compound to the plant is performed by foliage application, soil irrigation, seed disinfection or smoking.

2. The method according to claim 1, wherein, in Formula (I), $R^1$ and $R^2$ represent a hydrogen atom, and $R^3$ and $R^4$ each independently represents a hydrogen atom, —$SO_3H$, —$PO_3H_2$, a glycoysyl group or —$COR^{11}$, wherein $R^{11}$ represents an unsubstituted or substituted C1-30 alkyl group, or an unsubstituted or substituted C2-30 alkenyl group.

3. The method according to claim 1, wherein, in Formula (I), $R^1$ is —$COR^{11}$ wherein $R^{11}$ represents an unsubstituted or substituted C1-30 alkyl group, or an unsubstituted or substituted C2-30 alkenyl group, and $R^2$ to $R^4$ represent a hydrogen atom.

4. The method according to claim 1, wherein the application of the compound is performed by foliage application.

5. The method according to claim 1, wherein the plant is soil-cultured.

6. The method according to claim 1, wherein the compound is applied as a composition which further comprises a surfactant.

7. The method according to claim 1, wherein the compound is applied as a composition which further comprising a spreading agent.

8. The method according to claim 1, wherein the amount of the compound used is 2 to 20 mM.

9. The method according to claim 1, wherein the plant is infected with the plant virus prior to application of the compound.

* * * * *